(12) United States Patent
Lin

(10) Patent No.: US 11,517,208 B2
(45) Date of Patent: Dec. 6, 2022

(54) SINGLE-ARM MICRO AIR-PRESSURE PUMP DEVICE

(71) Applicants: Shiming Lin, Taipei (TW); BIV MEDICAL, LTD., Caotun Township, Nantou County (TW)

(72) Inventor: Shiming Lin, Taipei (TW)

(73) Assignees: Shiming Lin, Taipei (TW); BIV MEDICAL, LTD., Nantou County (TW)

(*) Notice: Subject to any disclaimer, the term of this patent is extended or adjusted under 35 U.S.C. 154(b) by 783 days.

(21) Appl. No.: 16/465,498

(22) PCT Filed: Nov. 29, 2017

(86) PCT No.: PCT/CN2017/113534
§ 371 (c)(1),
(2) Date: May 30, 2019

(87) PCT Pub. No.: WO2018/099390
PCT Pub. Date: Jun. 7, 2018

(65) Prior Publication Data
US 2020/0060560 A1 Feb. 27, 2020

Related U.S. Application Data

(60) Provisional application No. 62/601,843, filed on Apr. 4, 2017, provisional application No. 62/497,747, filed
(Continued)

(51) Int. Cl.
*A61B 5/021* (2006.01)
*A61B 5/022* (2006.01)
(Continued)

(52) U.S. Cl.
CPC ........ *A61B 5/02141* (2013.01); *A61B 5/0225* (2013.01); *A61B 5/02208* (2013.01);
(Continued)

(58) Field of Classification Search
CPC ............ A61B 5/02141; A61B 5/02208; A61B 5/0225; A61B 5/361; A61B 5/681;
(Continued)

(56) References Cited

U.S. PATENT DOCUMENTS

| 4,931,000 A | 6/1990 | Fleming, Jr. |
|---|---|---|
| 2004/0141858 A1 | 7/2004 | Grant |

FOREIGN PATENT DOCUMENTS

| CN | 101608610 A | 12/2009 |
|---|---|---|
| CN | 201396261 Y | 2/2010 |

(Continued)

*Primary Examiner* — Devin B Henson
*Assistant Examiner* — Joseph A Tombers
(74) *Attorney, Agent, or Firm* — Muncy, Geissler, Olds & Lowe, P.C.

(57) ABSTRACT

A single-arm micro air-pressure pump device, having an air pump body and a driving unit. The air pump body includes a supporting frame, an air chamber unit coupled to a side of the supporting frame, and a swing arm provided on the air chamber unit. The driving unit is fixed on the supporting frame and has an output shaft. The output shaft is provided with an eccentric shaft and is configured to rotate the eccentric shaft, and the eccentric shaft has an end coupled to the output shaft and an opposite end coupled to the swing arm in order to drive the swing arm into a reciprocating motion between at least a proximal position and a distal position with respect to the air chamber unit. The reciprocating motion pushes a piston unit provided on one end of the swing arm and causes the air output.

11 Claims, 5 Drawing Sheets

Related U.S. Application Data on Dec. 1, 2016, provisional application No. 62/497,740, filed on Dec. 1, 2016.

(51) Int. Cl.
*A61B 5/00* (2006.01)
*A61B 5/0225* (2006.01)
*F04B 43/02* (2006.01)
*F04B 53/10* (2006.01)
*A61B 5/361* (2021.01)
*F04B 45/047* (2006.01)
*A61B 5/0235* (2006.01)

(52) U.S. Cl.
CPC .............. *A61B 5/361* (2021.01); *A61B 5/681* (2013.01); *F04B 43/02* (2013.01); *F04B 45/047* (2013.01); *F04B 53/10* (2013.01); *A61B 5/0235* (2013.01)

(58) Field of Classification Search
CPC ...... A61B 5/0235; F04B 43/02; F04B 45/047; F04B 53/10; F04B 39/121; F04B 39/123
See application file for complete search history.

(56) References Cited

FOREIGN PATENT DOCUMENTS

| | | | |
|---|---|---|---|
| CN | 201714639 U | | 1/2011 |
| CN | 202628470 U | | 12/2012 |
| CN | 204458282 U | * | 12/2014 |
| CN | 204458282 U | | 7/2015 |
| TW | I488609 B | | 6/2015 |

* cited by examiner

SINGLE-ARM MICRO AIR-PRESSURE PUMP DEVICE

BACKGROUND OF THE INVENTION

1. Technical Field

The present invention relates to a single-arm micro air-pressure pump device and more particularly to a single-arm micro air-pressure pump device for use with the cuff of a sphygmomanometer.

2. Description of Related Art

A micro air pump is a miniature gas delivery device whose working medium is gaseous and whose major applications are gas sampling, gas circulation, vacuum suction, vacuum retention, gas extraction, inflation, and pressurization, among others.

Micro air pumps can be divided by application into micro negative-pressure pumps, micro vacuum pumps, micro gas-circulation pumps, micro air pumps, micro gas-sampling pumps, micro inflation pumps, micro gas-extraction pumps, micro gas-extraction/inflation pumps, and so on; and by working principle into diaphragm pumps, electromagnetic pumps, centrifugal pumps, reciprocating pumps, and so on. Micro air pumps, in particular micro vacuum pumps, have been widely used in medical care, scientific research, laboratories, environmental protection, instruments, and the chemical industry. Compared with common air pumps, micro air pumps have such advantages as compactness, low noise, low power consumption, easy operation, portability, no need for maintenance, and the ability to work around the clock and work with mediums rich in water vapor.

Taiwan Invention Patent No. I488609, for example, discloses a conventional micro pump for use with a sphygmomanometer cuff, wherein the micro pump is a diaphragm pump including: a discharge valve that allows a gas to flow out of a pump room and prohibits the gas from flowing in the opposite direction; an air room into which the gas flowing out of the pump room through the discharge valve flows; a discharge port for discharging the gas from the diaphragm pump; and a through hole portion for limiting the quantity of the gas flowing toward the discharge port from the air room. The micro pump uses a plurality of diaphragms to change the pressure in the air room, and the diaphragms are simultaneously controlled by a motor-driven supporting portion. As the structure of this conventional micro pump cannot be easily downsized during manufacture, it is practically impossible to apply the bulky micro pump to a portable electronic device that is designed to be carried around. In short, the conventional micro pump still leaves room for improvement.

BRIEF SUMMARY OF THE INVENTION

The primary objective of the present invention is to provide a micro pump for use with a portable electronic device to enable blood pressure measurement wherever desired.

The present invention provides a single-arm micro air-pressure pump device, comprising an air pump body and a driving unit. The air pump body includes a supporting frame, an air chamber unit coupled to a side of the supporting frame, and a swing arm provided on the air chamber unit. The driving unit is fixed on the supporting frame and has an output shaft, wherein the output shaft is provided with an eccentric shaft and is configured to rotate the eccentric shaft, and the eccentric shaft has an end coupled to the output shaft and an opposite end coupled to the swing arm in order to drive the swing arm into a reciprocating motion between at least a proximal position and a distal position with respect to the air chamber unit. The air chamber unit includes a first air chamber, a second air chamber, and a third air chamber. The second air chamber and the third air chamber are provided on a side of the first air chamber. There are a first-direction check valve between the second air chamber and the first air chamber and a second-direction check valve between the third air chamber and the first air chamber. The swing arm has an end provided with a piston unit, and the piston unit covers the first-direction check valve and the second-direction check valve from above. Air is drawn from the second air chamber into the first air chamber when the swing arm is moved to the distal position, and the air is output from the first air chamber to the third air chamber and then discharged through an air outlet of the third air chamber when the swing arm is moved to the proximal position.

Furthermore, the output shaft of the driving unit is perpendicular to the swing arm.

Furthermore, the eccentric shaft has a first coupling portion and a second coupling portion at its two ends respectively. The first coupling portion is coupled to the output shaft, the second coupling portion is coupled to one end of the swing arm, and the first coupling portion is eccentrically provided with respect to the second coupling portion.

Furthermore, the piston unit has a bottom side provided with an air-guiding groove, and the air-guiding groove lies above the first-direction check valve and has a side integrally extended with an air cup. The air cup lies above the second-direction check valve, has a top end coupled to the swing arm, and has an interior space in communication with the air-guiding groove. When the swing arm is moved to the distal position, the air cup is stretched upward such that the air in the second air chamber flows into the interior space of the air cup through the air-guiding groove, and when the swing arm is moved to the proximal position, the air cup is pushed downward and thereby compresses the first air chamber such that the air in the first air chamber is output to the third air chamber through the second-direction check valve.

Furthermore, the air chamber unit includes a first layer, a second layer, and a third layer. The first air chamber is provided between the first layer and the second layer, and the second air chamber and the third air chamber are provided between the second layer and the third layer.

Furthermore, the first layer is integrally formed with the supporting frame and constitutes a co-constructed body.

Furthermore, the second layer and/or the third layer are provided with one or more grooves surrounding the second air chamber and the third air chamber, and an elastic gasket is provided between the second layer and the third layer and is positioned in the grooves to seal the second air chamber and the third air chamber hermetically.

Furthermore, the third layer is provided with an air output tube in communication with the third air chamber.

Furthermore, each of the first layer, the second layer, and the third layer has one or more positioning portions in the peripheral region, and the positioning portions correspond to one another so that a locking unit can be passed therethrough.

Furthermore, the third layer is provided with an air inlet in communication with the second air chamber.

Furthermore, the second air chamber is provided therein with one or two or more baffle walls.

Comparing to the conventional techniques, the present invention has the following advantages:

1. The present invention is distinguished from the prior art by its effective miniaturization and applicability to a wearable or portable device.

2. The present invention is also distinguished from the prior art by its higher air output efficiency and lower noise.

3. A secondary technical feature of the present invention is the two baffle walls in the second air chamber. The baffle walls are configured to increase the pressure of the output airflow so that the air pumped into an external device will not leak by flowing backward.

BRIEF DESCRIPTION OF THE SEVERAL VIEWS OF THE DRAWINGS

FIG. 4-1 shows the state (I) of use of the single-arm micro air-pressure pump device of the present invention.

FIG. 4-2 shows the state (II) of use of the single-arm micro air-pressure pump device of the present invention.

DETAILED DESCRIPTION OF THE INVENTION

Figure 1:
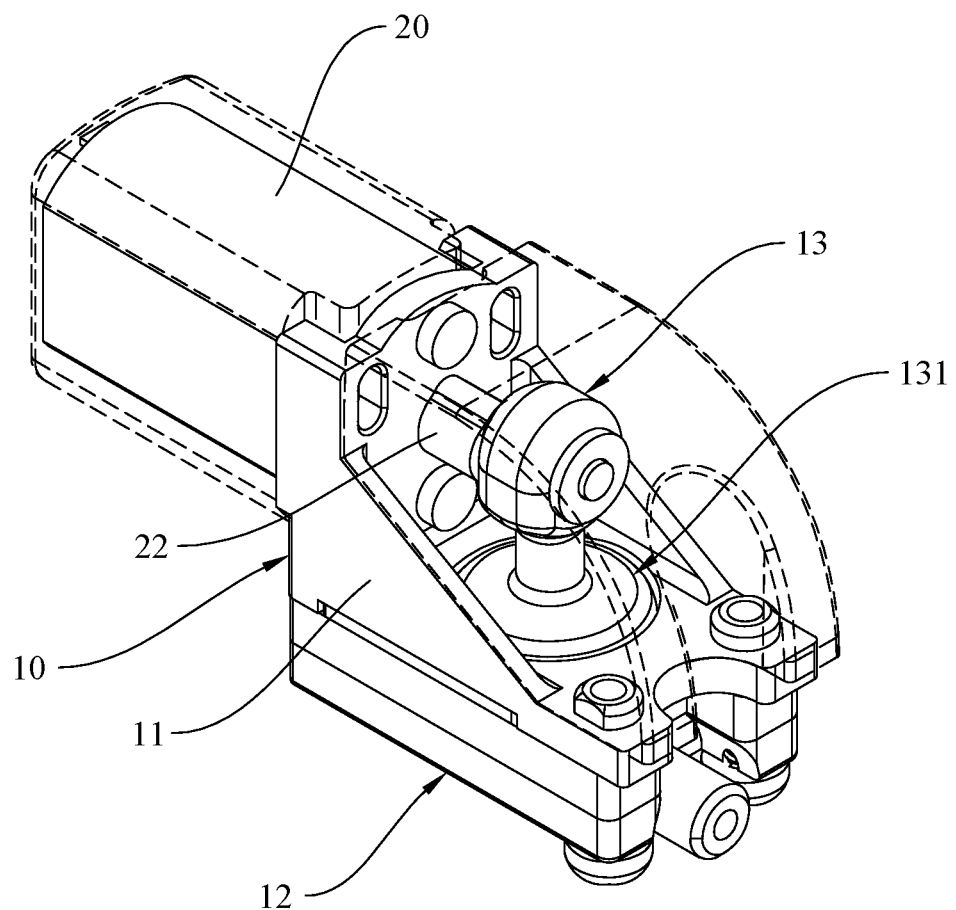
FIG. 1 is an assembled perspective view of the single-arm micro air-pressure pump device of the present invention.

The details and technical solution of the present invention are hereunder described with reference to accompanying drawings.

The present invention provides a single-arm micro air-pressure pump device configured for use with a wearable electronic device such as a smartwatch, health bracelet, arm sling, or other similar wearable device. In one preferred embodiment, and by way of example only, the single-arm micro air-pressure pump device is provided in/on a portable device and therefore can be easily carried around along with the portable device. The single-arm micro air-pressure pump device can be used in conjunction with an inflatable sphygmomanometer cuff so that, once the cuff is wrapped around a user's arm and air is pumped into the cuff to distend the bladder therein, a pressure sensor can detect the pressure variation in the bladder, allowing the user's systolic pressure and diastolic pressure to be known by analyzing the waveform of the variation.

The structural details of the single-arm micro air-pressure pump device of the present invention will be described below with reference to FIG. 1 to FIG. 3, which show an assembled perspective view and two exploded perspective views of the single-arm micro air-pressure pump device respectively.

The single-arm micro air-pressure pump device 100 essentially includes an air pump body 10 and a driving unit 20 provided on one side of the air pump body 10.

The air pump body 10 essentially includes a supporting frame 11, an air chamber unit 12 coupled to one side of the supporting frame 11, and a swing arm 13 provided on the air chamber unit 12. The driving unit 20 is fixed on the supporting frame 11 and has an output shaft 21 provided with an eccentric shaft 22. The eccentric shaft 22 has one end coupled to the output shaft 21 and the opposite end coupled to the swing arm 13. When the output shaft 21 is rotated, the eccentric shaft 22 is rotated together with the output shaft 21 and thereby drives the swing arm 13 into a reciprocating motion between at least two positions, e.g., a proximal position and a distal position, with respect to the air chamber unit 12. The driving unit 20 is preferably a direct-current motor, alternating-current motor, or other similar power element.

The eccentric shaft 22 has a first coupling portion 221 and a second coupling portion 222 at its two ends respectively. The first coupling portion 221 is coupled to the output shaft 21, and the second coupling portion 222 is coupled to one end of the swing arm 13. The first coupling portion 221 is eccentrically provided with respect to the second coupling portion 222 so that, when the first coupling portion 221 is rotated at a relatively fixed position, the second coupling portion 222 at the opposite end of the eccentric shaft 22 is moved along a circular path whose center is defined by the first coupling portion 221. The output shaft 21 of the driving unit 20 is perpendicular to the swing arm 13. The aforesaid distal position and proximal position of the swing arm 13 are two end-point positions of the swing arm 13 in a direction perpendicular to the air chamber unit 12 (corresponding to the upper end-point position and the lower end-point position in FIG. 4-1 and FIG. 4-2).

The air chamber unit 12 includes a first air chamber 12A, a second air chamber 12B, and a third air chamber 12C, the latter two of which are provided on one side of the first air chamber 12A. A first-direction check valve 121A is provided between the second air chamber 12B and the first air chamber 12A, and a second-direction check valve 122A is provided between the third air chamber 12C and the first air chamber 12A. The first-direction check valve 121A is opened when the air pressure in the second air chamber 12B is higher than that in the first air chamber 12A, and is closed when the air pressure in the second air chamber 12B is lower than that in the first air chamber 12A. The second-direction check valve 122A works the other way around. More specifically, the second-direction check valve 122A is opened when the air pressure in the first air chamber 12A is higher than that in the third air chamber 12C, and is closed when the air pressure in the first air chamber 12A is lower than that in the third air chamber 12C. The swing arm 13 is provided with a piston unit 131 at one end. The piston unit 131 covers the first-direction check valve 121A and the second-direction check valve 122A from above. When the swing arm 13 is moved to the distal position, air is drawn from the second air chamber 12B into the first air chamber 12A, and when the swing arm 13 is moved to the proximal position, air is output from the first air chamber 12A to the third air chamber 12C and then discharged through the air outlet of the third air chamber 12C. Thus, the extraction and discharge of air are completed through the operation of a single swing arm 13.

The structure of the present invention will be described in more detail below with reference to FIG. 1 to FIG. 3. It should be pointed out, however, that the structure disclosed herein serves only as a feasible preferred embodiment of the invention and is not intended to be restrictive of the scope of the invention.

In this preferred embodiment, the air chamber unit 12 is composed of a plurality of components and essentially includes a first layer 121, a second layer 122, and a third layer 123. The first layer 121 is integrally formed with the supporting frame 11 in order for the resulting co-constructed body to support the driving unit 20 and ensure the required relative positions of the driving unit 20 and the air chamber unit 12. The first air chamber 12A is provided between the first layer 121 and the second layer 122, and the second air chamber 12B and the third air chamber 12C are provided between the second layer 122 and the third layer 123.

The second layer 122 and the third layer 123 are provided with one or more grooves 1221 and 1231 surrounding the second air chamber 12B and the third air chamber 12C. An elastic gasket 124 is provided between the second layer 122 and the third layer 123 and is positioned in the grooves 1221 and 1231 to seal the second air chamber 12B and the third air chamber 12C hermetically. In another preferred embodiment, only one of the grooves 1221 and 1231 is provided in the second layer 122 or the third layer 123; the present invention has no limitation on the number or location of the grooves. Each of the first layer 121, the second layer 122, and the third layer 123 has one or more positioning portions 1212, 1222, or 1232 in the peripheral region. The positioning portions 1212, 1222, and 1232 correspond to one another so that a locking unit T can be passed therethrough. Once the locking unit T is locked in place, the elastic gasket 124, which surrounds the second air chamber 12B and the third air chamber 12C, is pressed tightly between the second layer 122 and the third layer 123 to produce an airtight seal.

The second air chamber 12B is provided therein with two baffle walls 121B. In the embodiment illustrated herein, the baffle walls 121B are provided on the second layer 122 and are slightly spaced apart from the third layer 123 to allow passage of air through the second air chamber 12B. In another preferred embodiment, the baffle walls 121B may be provided on the third layer 123 and spaced apart from the second layer 122 instead to meet structural design requirements (e.g., to enable easy unmolding or easy assembly). In yet another preferred embodiment, there may be one or more than two baffle walls 121B in the second air chamber 12B; the present invention has no limitation on the number of the baffle walls. According to the Bernoulli's principle, an airflow that flows from the air inlet of the second air chamber 12B to the air outlet of the second air chamber 12B will have a lower final velocity than the initial velocity because of the baffle walls 121B, resulting in a pressure increase of the output air. Thus, when the single-arm micro air-pressure pump device 100 is used to pump air into an external bladder, the air in the bladder will be effectively kept from flowing back to the pump device through the air inlet of the bladder.

The bottom side of the piston unit 131 is provided with an air-guiding groove 1311. The air-guiding groove 1311 lies above the first-direction check valve 121A and is extended on one side with an air cup 1312. The air cup 1312 is integrally formed with the air-guiding groove 1311 and lies above the second-direction check valve 122A. The top end of the air cup 1312 is coupled to the swing arm 13, and the interior space of the air cup 1312 is in communication with the air-guiding groove 1311. The top side of the first layer 121 is provided with an opening 1211 corresponding to the air cup 1312. The opening 1211 allows passage of the swing arm 13 and provides a space through which the air cup 1312 can be stretched. The air cup 1312 and the air-guiding groove 1311 of the piston unit 131 are formed of a single sheet of silicone or rubber (i.e., constitute a co-constructed unit) and are secured in position between the first layer 121 and the second layer 122. The co-constructed unit including the air-guiding groove 1311 and the air cup 1312 covers the first-direction check valve 121A and the second-direction check valve 122A from above. The volume of the first air chamber 12A is defined by the interior space of the air-guiding groove 1311 and of the air cup 1312.

The third layer 123 is provided with an air inlet 1233 in communication with the second air chamber 12B and an air output tube 1234 in communication with the third air chamber 12C. The air inlet 1233 serves to balance the internal pressure and external pressure of the second air chamber 12B, ensuring that air can be guided through the second air chamber 12B into the first air chamber 12A. The air output tube 1234 is configured to couple with a sphygmomanometer cuff (not shown) and inflate the bladder in the cuff by delivering the air in the third air chamber 12C to the bladder.

Figure 2:
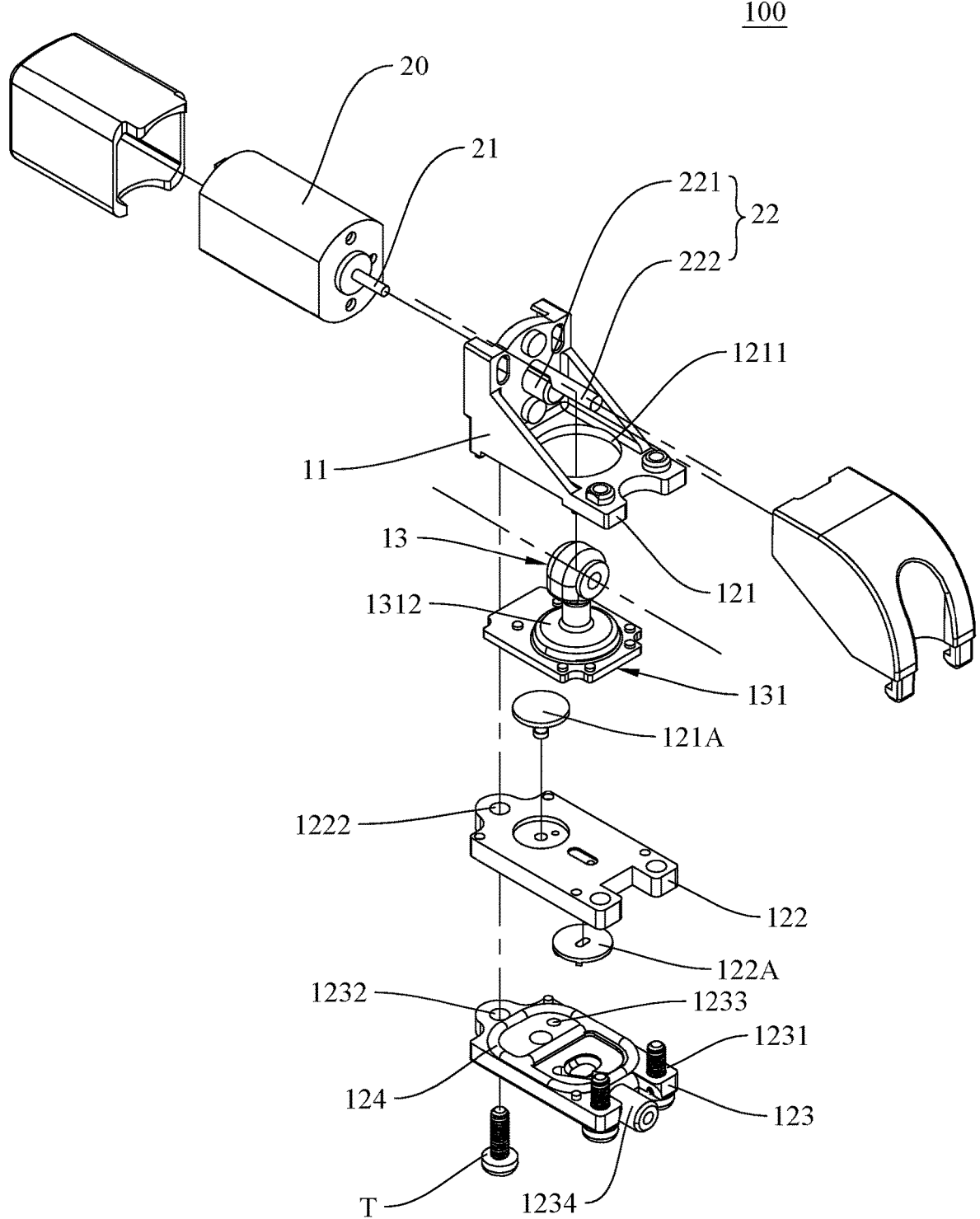
FIG. 2 is the exploded perspective view (I) of the single-arm micro air-pressure pump device of the present invention.
Figure 3:
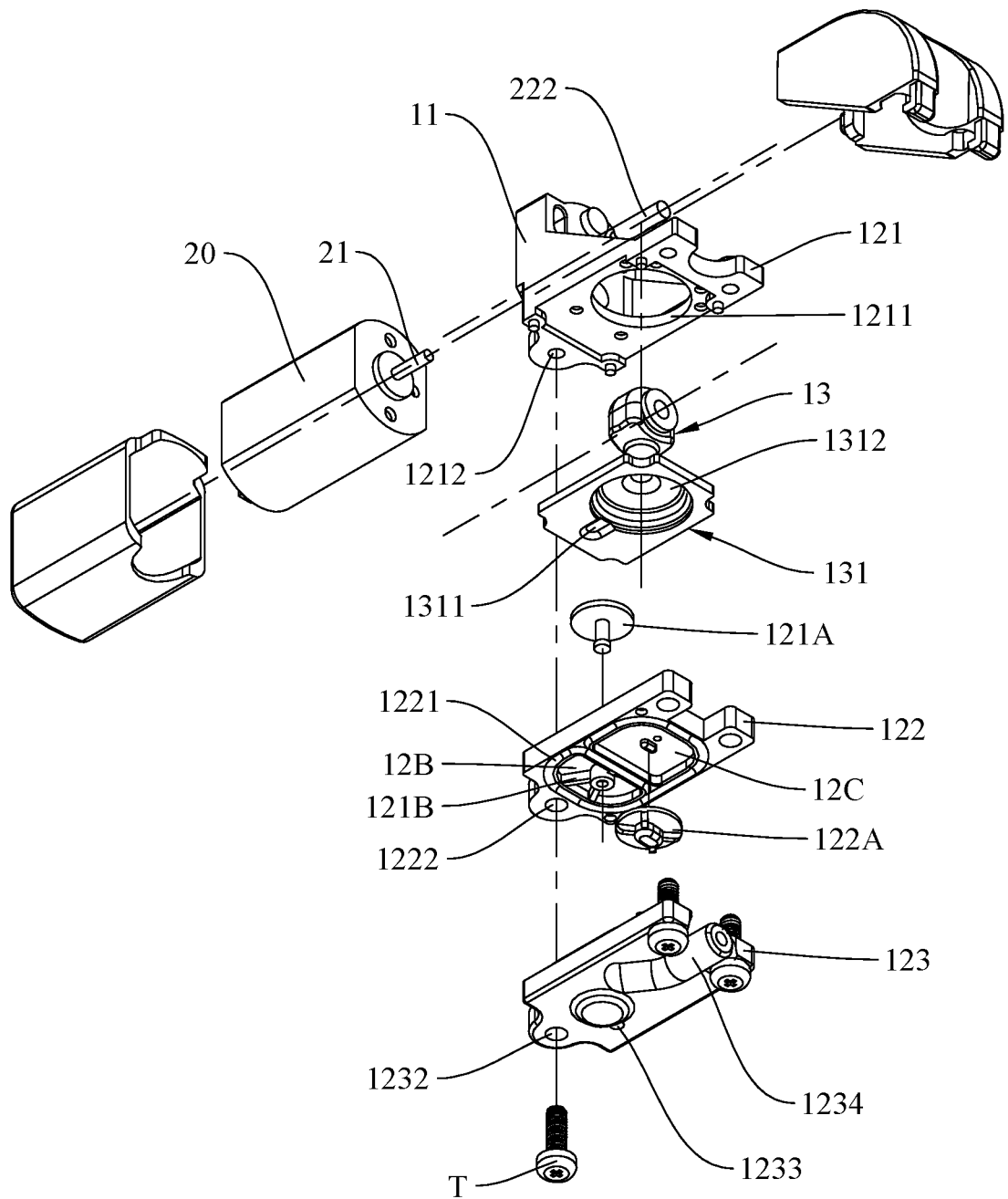
FIG. 3 is the exploded perspective view (II) of the single-arm micro air-pressure pump device of the present invention.
Figures 1, 4:
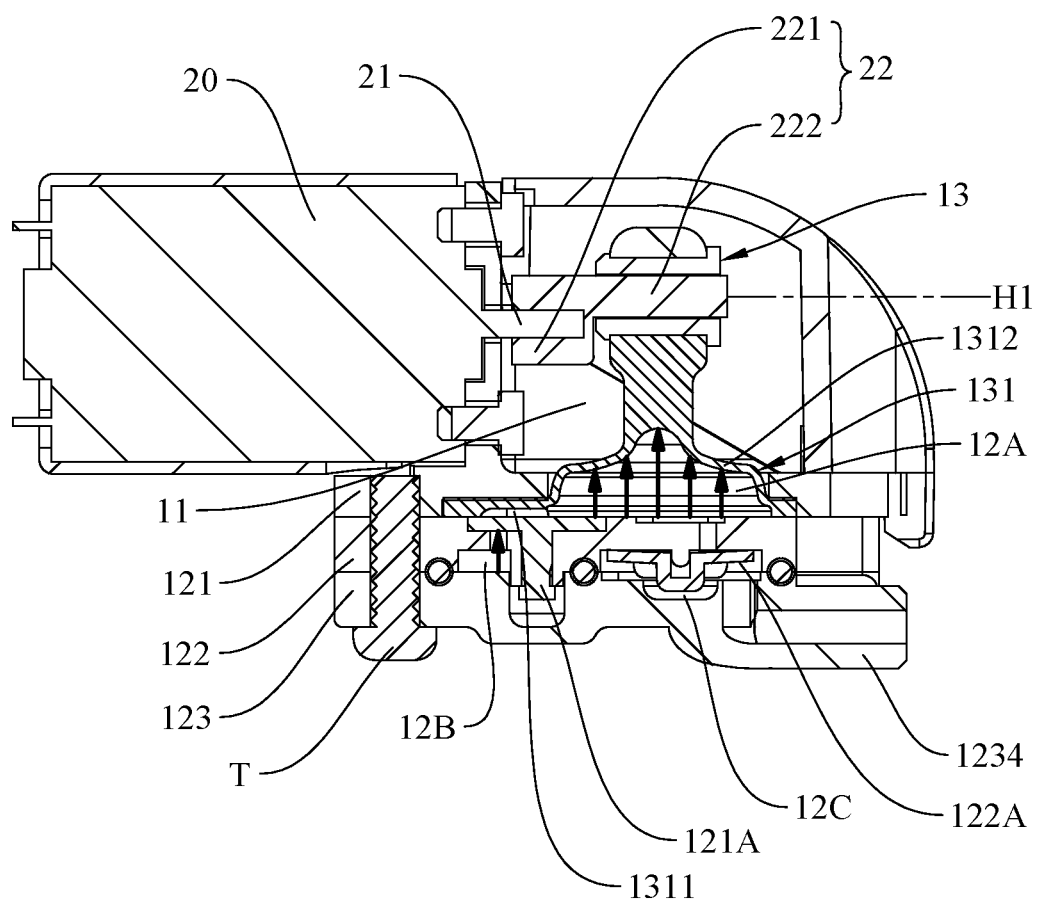
Figures 2, 4:
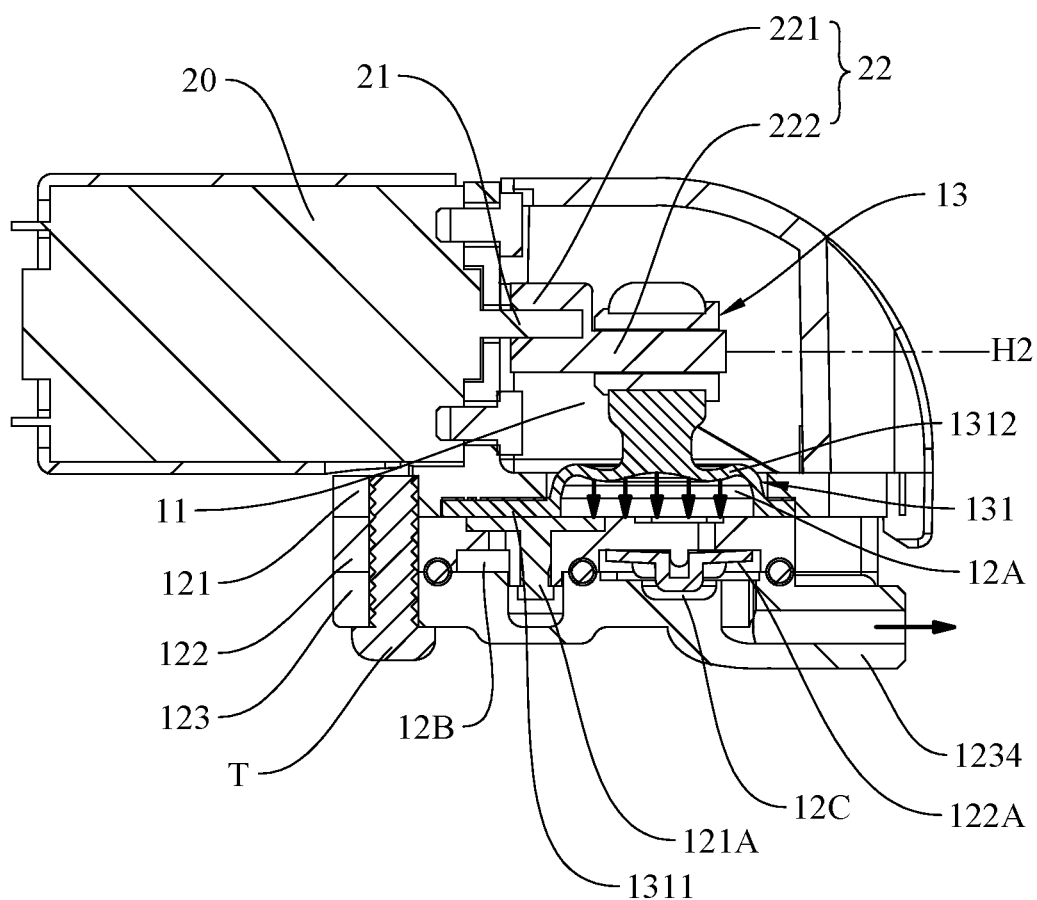

Please refer now to FIG. 4-1 and FIG. 4-2, which show two states of use of the single-arm micro air-pressure pump device of the present invention respectively.

Once the single-arm micro air-pressure pump device 100 is activated, referring to FIG. 4-1, the driving unit 20 moves the second coupling portion 222 of the eccentric shaft 22 along a circular path and thereby brings the swing arm 13 to the distal position H1. When the swing arm 13 arrives at the distal position H1, the air cup 1312 is stretched upward such that the air pressure in the second air chamber 12B is higher than that in the first air chamber 12A; consequently, the air in the second air chamber 12B pushes open the first-direction check valve 121A and flows into the interior space of the air cup 1312 through the air-guiding groove 1311 (i.e., enters the first air chamber 12A). At this moment, the second-direction check valve 122A is closed because the pressure in the third air chamber 12C is higher than that in the first air chamber 12A. When the second coupling portion 222 of the eccentric shaft 22 is further moved along the circular path and thereby brings the swing arm 13 to the proximal position H2, as shown in FIG. 4-2, the air cup 1312 is pushed downward and hence compresses the first air chamber 12A. The first-direction check valve 121A is now closed because the air pressure in the first air chamber 12A is higher than that in the second air chamber 12B, and the air in the first air chamber 12A pushes open the second-direction check valve 122A and is output to the third air chamber 12C because the air pressure in the first air chamber 12A is higher than that in the third air chamber 12C.

According to the above, the present invention is distinguished from the prior art by its effective miniaturization and applicability to a wearable or portable device. In addition, the present invention is also distinguished from the prior art by its higher air output efficiency and lower noise. Furthermore, a secondary technical feature of the present invention is the two baffle walls in the second air chamber. The baffle walls are configured to increase the pressure of the output airflow so that the air pumped into an external device will not leak by flowing backward.

The above is the detailed description of the present invention. However, the above is merely the preferred embodiment of the present invention and cannot be the limitation to the implement scope of the present invention, which means the variation and modification according to the present invention may still fall into the scope of the invention.

What is claimed is:

1. A single-arm micro air-pressure pump device, comprising:

an air pump body including a supporting frame, an air chamber unit coupled to a side of the supporting frame, and a swing arm provided on the air chamber unit; and a driving unit fixed on the supporting frame and having an output shaft, wherein the output shaft is provided with an eccentric shaft and is configured to rotate the eccentric shaft, and the eccentric shaft has an end coupled to the output shaft and an opposite end coupled to the swing arm in order to drive the swing arm into a reciprocating motion between at least a proximal position and a distal position with respect to the air chamber unit;

wherein the air chamber unit includes a first air chamber, a second air chamber, and a third air chamber, the second air chamber and the third air chamber are provided on a side of the first air chamber, there are a first-direction check valve between the second air chamber and the first air chamber and a second-direction check valve between the third air chamber and the first air chamber, the swing arm has an end provided with a piston unit, the piston unit covers the first-direction check valve and the second-direction check valve from above, the piston unit comprises an air cup, and an extending sheet surrounding the air cup, the air cup comprises an interior space, a bottom side of the extending sheet is provided with an air-guiding groove in communication with the interior space, the air-guiding groove is narrower than the interior space and lies above the first-direction check valve, the air cup lies above the second-direction check valve and has a top end coupled to the swing arm, when the swing arm is moved to the distal position, air is drawn from the second air chamber into the first air chamber, and when the swing arm is moved to the proximal position, the air-guiding groove is compressed so that an inner wall surface of the air-guiding groove is pressed against the first direction check valve to output the air from the first air chamber to the third air chamber and then discharged through an air outlet of the third air chamber when the swing arm is moved to the proximal position.

2. The single-arm micro air-pressure pump device of claim 1, wherein the output shaft of the driving unit is perpendicular to the swing arm.

3. The single-arm micro air-pressure pump device of claim 2, wherein the eccentric shaft has a first coupling portion and a second coupling portion at its two ends respectively, the first coupling portion is coupled to the output shaft, the second coupling portion is coupled to one end of the swing arm, and the first coupling portion is eccentrically provided with respect to the second coupling portion.

4. The single-arm micro air-pressure pump device of claim 1, wherein when the swing arm is moved to the distal position, the air cup is stretched upward such that the air in the second air chamber flows into the interior space of the air cup through the air-guiding groove, and when the swing arm is moved to the proximal position, the air cup is pushed downward and thereby compresses the first air chamber such that the air in the first air chamber is output to the third air chamber through the second-direction check valve.

5. The single-arm micro air-pressure pump device of claim 1, wherein the air chamber unit includes a first layer, a second layer, and a third layer, the first air chamber is provided between the first layer and the second layer, and the second air chamber and the third air chamber are provided between the second layer and the third layer.

6. The single-arm micro air-pressure pump device of claim 5, wherein the first layer is integrally formed with the supporting frame and constitutes a co-constructed body.

7. The single-arm micro air-pressure pump device of claim 5, wherein the second layer and/or the third layer are provided with one or more grooves surrounding the second air chamber and the third air chamber, and an elastic gasket is provided between the second layer and the third layer and is positioned in the grooves to seal the second air chamber and the third air chamber hermetically.

8. The single-arm micro air-pressure pump device of claim 5, wherein the third layer is provided with an air output tube in communication with the third air chamber.

9. The single-arm micro air-pressure pump device of claim 5, wherein each of the first layer, the second layer, and the third layer has one or more positioning portions in the peripheral region, and the positioning portions correspond to one another so that a locking unit can be passed therethrough.

10. The single-arm micro air-pressure pump device of claim 5, wherein the third layer is provided with an air inlet in communication with the second air chamber.

11. The single-arm micro air-pressure pump device of claim 1, wherein the second air chamber is provided therein with one or two or more baffle walls the baffle wall protrudes downward from the inner top surface of the second air chamber and is spaced apart from the inner bottom surface of the second air chamber, or protrudes upward from the inner bottom surface of the second air chamber and is spaced apart from the inner top surface of the second air chamber.

* * * * *